United States Patent [19]
Saito et al.

[11] Patent Number: 6,100,403
[45] Date of Patent: Aug. 8, 2000

[54] PRODUCTION OF BENZALDEHYDE COMPOUNDS

[75] Inventors: Yuzuru Saito, Yamaguchi; Hideya Mizufune; Makoto Yamashita, both of Hyogo, all of Japan

[73] Assignee: Takeda Chemical Industries, Ltd., Osaka, Japan

[21] Appl. No.: 09/292,384

[22] Filed: Apr. 12, 1999

Related U.S. Application Data

[62] Division of application No. 08/880,638, Jun. 23, 1997, Pat. No. 5,952,509.

[30] Foreign Application Priority Data

Jun. 27, 1996 [JP] Japan .................................. 8-167862

[51] Int. Cl.[7] .................................................. C07D 417/00
[52] U.S. Cl. ........................................ 546/269.7; 546/340
[58] Field of Search ................................ 546/340, 269.7

[56] References Cited

FOREIGN PATENT DOCUMENTS

| 0 193 256 A1 | 9/1986 | European Pat. Off. . |
| 0 257 781 A1 | 3/1988 | European Pat. Off. . |
| 0 506 273 A2 | 9/1992 | European Pat. Off. . |
| 92/18501 | 10/1992 | WIPO . |

OTHER PUBLICATIONS

Y. Momose et al. "Studies on Antidiabetic Agents. X.[1]) Synthesis and Biological Activities of Pioglitazone and Related Compounds", Chem. Pharm. Bull., vol. 39, No. 6, pp. 1440–1445, 1991.

*Primary Examiner*—Zinna Northington Davis
*Attorney, Agent, or Firm*—Wenderoth, Lind & Ponack, LLP.

[57] ABSTRACT

A method of producing a compound represented by the formula:

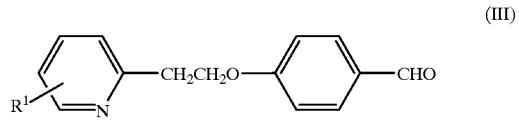

(III)

wherein $R^1$ stands for hydrogen or an optionally substituted alkyl or acyl group, which comprises reacting a compound represented by the formula:

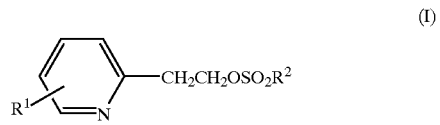

(I)

wherein $R^1$ is of the same meaning as defined above, and $R^2$ stands for an optionally halolgenated alkyl group or an optionally substituted phenyl group with a compound represented by the formula:

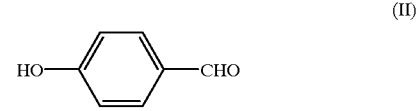

(II)

in a lower alcohol in the presence of an alkali metal or alkaline earth metal carbonate; the compound (III) being useful as starting compounds for producing thiazolidinedione derivatives having hypoglycemic and hypolipidemic activities.

57 Claims, No Drawings

PRODUCTION OF BENZALDEHYDE COMPOUNDS

This application is a divisional application of Ser. No. 08/880,638, filed Jun. 23, 1997, now U.S. Pat. No. 5,952,509.

FIELD OF THE INVENTION

This invention relates to a novel method of producing a 4-[2-(2-pyridyl)ethoxy]benzaldehyde compound (hereinafter simply abbreviated as "benzaldehyde compound") which is useful as a starting compound of synthesizing thiazolidinedione derivatives having hypoglycemic and hypolipidemic activities.

BACKGROUND OF THE INVENTION

In JP-A S61(1986)-267580 (EP-A 193256), JP-A H5(1993)-086057 (WO-A 9218501) and Chem. Pharm. Bull., 39, 1440(1991), there are descriptions that thiazolidinedione derivatives having various 2-(2-pyridyl) ethoxy groups show hypoglycemic and hypolipidemic activity and they are useful as medicines.

Methods of producing such thiazolidinedione derivatives as above, those described in, for example, (1) JP-A S63 (1988)-139182 (EP-A 257781), (2) Chem. Pharm. Bull., 39, 1440(1991) or (3) JP-A H5(1993)-112483 (EP-A 506273) are known.

In the above-mentioned (1), as a method of producing a benzaldehyde compound, the starting compound of the above-described thiazolidinedione derivatives, there is described a method which comprises allowing 2-(2-pyridyl) ethyl alkane (or allene) sulfonate compound to react with p-hydroxybenzaldehyde in a solvent as exemplified by aliphatic halogenated hydrocarbons, aromatic hydrocarbons, ethers, water, ethyl acetate and dimethylformamide, or in a suitable mixture of them in the presence of a base. When the reaction is conducted in a non-aqueous organic solvent, among these solvents, it takes a relatively long period of time for completing the reaction. Due to β-elimination reaction as the side reaction, 2-vinyl pyridine is produced prevalently to lower the yield and purity of the object benzaldehyde compound, exerting undesirable influence on the yield and quality of the products in the subsequent reaction steps. On the other hand, in the case of conducting the reaction in the two-layer system of the above organic solvent and water, it is necessary to allow a phase-transfer catalyst to exist in the reaction system. Since the solvent employed is not homogeneous, control of stirring conditions is difficult to make the yield and purity of the object benzaldehyde compound relatively low, thus the method disclosed in (1) above is hardly considered industrially advantageous one.

Likewise, in the method described in the above (2), since the reaction is conducted in the two-layer system of methylene chloride and water, use of benzyl tributyl ammonium chloride is required as a phase-transfer catalyst. Since the solvent employed is not homogeneous, control of stirring conditions is difficult, and the method can hardly considered industrially advantageous one.

In the method described in the above (3), since an alkali metal salt or alkaline earth metal salt of p-hydroxybenzaldehyde is employed as a starting compound, a step for isolating such a starting compound in advance is required.

Therefore, it has been desired to provide a more convenient method of producing benzaldehyde compounds useful as starting compounds for synthesizing thiazolidinedione derivatives showing hypoglycemic and hypolipidemic activity in a higher yield and quality.

SUMMARY OF THE INVENTION

Under such circumstances as above, the present inventors have conducted diligent studies to find that the object benzaldehyde compounds can be produced in a high yield and quality and conveniently by employing, as the reaction solvent, lower alcohols and a mixture solvent of such a lower alcohol with another organic solvent.

Namely, the present invention relates to a method of producing a compound represented by the formula:

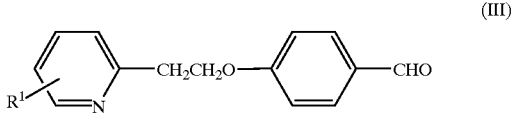

(III)

wherein $R^1$ stands for hydrogen or an optionally substituted alkyl or acyl group, which comprises reacting a compound represented by the formula:

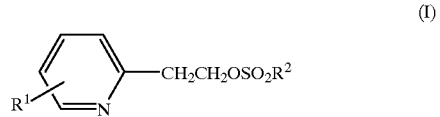

(I)

wherein $R^1$ is of the same meaning as defined above, and $R^2$ stands for an optionally halolgenated alkyl group or an optionally substituted phenyl group with a compound represented by the formula:

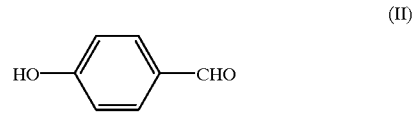

(II)

in a lower alcohol in the presence of an alkali metal or alkaline earth metal carbonate.

DETAILED DESCRIPTION OF THE INVENTION

Examples of the alkyl group in the "optionally substituted alkyl group" shown by $R^1$ in the formulae (I) and (III) include $C_{1-4}$ straight-chain or branched alkyl groups such as methyl, ethyl, n-propyl, isopropyl, n-butyl, isobutyl and t-butyl. As the alkyl group, methyl and ethyl are preferable, especially ethyl is preferable.

Examples of the acyl group in the "optionally substituted acyl group" shown by $R^1$ include $C_{1-4}$ alkanoyl groups such as formyl, acetyl, propionyl, butyryl and isobutyryl. As the acyl group, formyl and acetyl are preferable, especially acetyl is preferable.

And, examples of the substituents in the "optionally substituted alkyl group" and "optionally substituted acyl group" include optionally protected hydroxyl groups and optionally protected carboxyl groups.

As the hydroxyl- or carboxyl-protecting group, any one can be employed so long as it does not exert any undesirable effect on the reaction, which is exemplified by those described in, e.g. "Protective Groups in Organic Synthesis, the second edition" authored by Greene-Wats, John Wiley, (1991). Specifically, as the hydroxyl-protecting group, use is made of, for example, methoxymethyl, methoxyethoxymethyl, trimethyl silyl, t-butyl dimethyl silyl, 2-tetrahydropyranyl, benzyl and p-nitrobenzyl; and as the carboxyl-protecting group, use is made of, for example, methoxymethyl, methoxyethoxymethyl, trityl, benzhydryl, benzyl, p-nitrobenzyl and t-butyl.

$R^1$ is preferably hydrogen or a $C_{1-4}$ alkyl group, more preferably ethyl. The position on which $R^1$ is substituted may be any of 3-, 4-, 5- or 6-position of the pyridine ring, preferably 5-position. Especially preferable $R^1$ is 5-ethyl group.

In the formula (I), as the alkyl group in the "optionally halogenated alkyl groups" shown by $R^2$, use is made of the same ones in $R^1$ described above. And, as the halogen atom in the "optionally halogenated alkyl groups" shown by $R^2$, mention is made of, for example, chlorine, fluorine and bromine.

As the substituent in the "optionally substituted phenyl group" shown by $R^2$, mention is made of, for example, $C_{1-3}$ alkyl groups (e.g. methyl, ethyl, n-propyl, isopropyl), $C_{1-3}$ alkoxy groups (e.g. methoxy, ethoxy, propoxy, isopropoxy), nitro group and halogen atoms (e.g. chlorine, fluorine, bromine). The said substituent is preferably $C_{1-3}$ alkyl groups, more preferably methyl group.

$R^2$ is preferably 1) $C_{1-4}$ alkyl groups or 2) phenyl group optionally substituted with a $C_{1-3}$ alkyl group; more preferably methyl group or p-tolyl group; especially preferably methyl group.

In the method of this invention, the lower alcohol employable as the reaction solvent includes $C_{1-4}$ straight-chain or branched alcohol, for example, methanol, ethanol, 1-propanol, 2-propanol, 1-butanol, 2-butanol, 2-methyl-1-propanol and 2-methyl-2-propanol. Preferable examples of the said lower alcohol include $C_{1-3}$ straight-chain or branched alcohol. Use of these $C_{1-3}$ straight-chain or branched alcohol also facilitates operations in the subsequent condensation of a reaction mixture containing the compound (III) obtained after the reaction. The lower alcohol is more preferably methanol, ethanol or 2-propanol; especially preferably ethanol or 2-propanol.

The volume of the lower alcohol to be employed ranges, relative to one weight part of the compound (I), usually from 3 to 50 weight parts, preferably from 3 to 30 weight parts, especially preferably from 3 to 20 weight parts.

In the present invention, the reaction may optionally be conducted in the co-existence of an organic solvent other than alcohol (hereinafter sometimes simply referred to as "organic solvent"). As the organic solvent, any organic solvent which does not adversely effect the reaction can be employed. Examples of these solvents include for example, aromatic hydrocarbons such as benzene, toluene and xylene; aliphatic hydrocarbons such as hexane, pentane and heptane; esters such as ethyl acetate and butyl acetate; ethers such as diethyl ether, diisopropyl ether, t-butyl methyl ether, tetrahydrofuran and dioxane; ketones such as acetone, methyl ethyl ketone and methyl isobutyl ketone; aliphatic halogenated hydrocarbons such as methylene chloride, chloroform and ethane dichloride; nitriles such as acetonitrile; and amides such as N,N-dimethylformamide. The said organic solvents include preferably aromatic hydrocarbons, aliphatic hydrocarbons, esters, ethers, ketones, nitriles or amides; more preferably toluene, hexane, ethyl acetate, diisopropyl ether or t-butyl methyl ether; especially preferably toluene or ethyl acetate.

When the reaction is conducted in the co-existence of the organic solvent other than alcohol, a mixture of a lower alcohol and the organic solvent in an optional ratio can be employed. In this case, the lower alcohol in the total solvent (a mixture of the lower alcohol and an organic solvent other than alcohol) is used in a ratio of not less than 30 volume %, preferably not less than 40 volume %, especially preferably not less than 50 volume %, relative to the total solvent. And, the volume of the mixture solvent of a lower alcohol and the organic solvent is substantially the same as that when the above-mentioned lower alcohol is used singly. Incidentally, the time of adding organic solvent is not specifically restricted.

In the present invention, as the alkali metal or alkaline earth metal carbonate (hereinafter simply referred to as "carbonate"), mention is made of potassium carbonate, sodium carbonate, calcium carbonate, magnesium carbonate, sodium hydrogencarbonate and potassium hydrogencarbonate. The said carbonate is preferably the carbonate of an alkali metal. As the alkali metal carbonate, potassium carbonate is preferably mentioned.

The amount of the carbonate to be employed ranges from usually 1 to 5, preferably 1 to 3, especially preferably 1 to 2 times mol. as much, relative to the compound (I).

In the present invention, the amount of the compound (II), which is the starting compound, to be employed ranges from usually 1 to 5, preferably 1 to 3, especially preferably 1 to 2 times mol. as much, relative to the compound (I).

The reaction temperature in the method of this invention ranges usually from 20 to 120° C., preferably from 50 to 100° C., especially preferably from 70 to 90° C.

The reaction time in the method of this invention ranges usually from 1 to 15 hours, preferably from 1 to 10 hours.

In the present invention, the reaction is conducted preferably in the presence of water. In this case, the volume ratio of water to the solvent (the solvent using a lower alcohol singly, or a mixture of a lower alcohol and the organic solvent) ranges, for example, from 1 to 10 volume %, preferably from 1 to 5 volume %. And, the time of adding water is not specifically restricted.

In the case where the method of this invention is conducted, for example, on an industrial scale, i.e. on a scale of treating a relatively large amount, since the starting compound is used in a relatively high concentration, it is often the case that the fluidity of the reaction mixture is reduced to make the control of stirring conditions difficult. In such a case as above, addition of water to the reaction system improves the fluidity of the reaction mixture to make the control of stirring conditions easy. As a result, even when the reaction is conducted in a relatively large scale, a relatively high yield and purity of the object compound can be maintained.

In the method of this invention, especially the reaction is preferably conducted at 70 to 90° C., in a solvent comprising ethanol or 2-propanol, in the presence of potassium carbonate with water added in an amount of 1 to 10 volume % relative to the solvent.

The compound (III) to be produced by the method of this invention can be isolated and purified by means of a conventional isolating and refining means such as concentration, concentration under reduced pressure, solvent-extraction, crystallization, phasic-transfer or chromatography.

In the method of this invention, since the compound (III) of a remarkably high quality is obtained, it can be used for the subsequent reaction without isolation and purification.

In the present invention, the compound (I), which is the starting compound, can be produced by the method described in, for example, JP-A S63(1988)-139182 (EP-A 257781) and JP-A H5(1993)-112483 (EP-A 506273).

The compound (III) produced by the method of this invention, e.g. 4-[2-(5-ethyl-2-pyridyl)ethoxy]benzaldehyde, can be led to a compound having hypoglycemic and hypolipidemic activities, e.g. 5-[4-[2-(5-ethyl-2-pyridyl)ethoxy]benzyl]-2,4-thiazolidinedione, by subjecting the compound (III), in accordance with the method described in, for example, JP-A S63(1988)-139182 (EP-A 257781), to condensation with 2,4-thiazolidinedione in the presence of a suitable base, then subjecting further the condensate to reduction.

In the following manner, compound (III) is subjected to condensation with 2,4-thiazolidinedione to produce compound (IV), which is then subjected to reduction to produce compound (V).

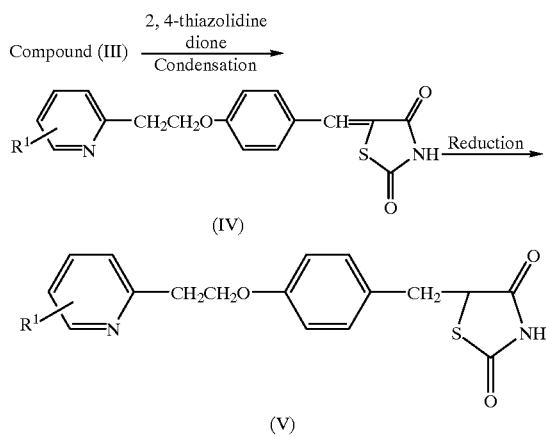

Condensation is carried out in the above-described lower alcohol or organic solvent in the presence of a base.

Examples of the base include amines such as ammonia, methylamine, ethylamine, butylamine, pyrrolidine, piperidine, morpholine, piperazine, diethylamine, diisopropylamine and triethylamine; sodium alkoxides such as sodium methoxide and sodium ethoxide; alkali metal carbonate such as potassium carbonate and sodium carbonate; alkali metal hydride such as sodium hydride; alkali metal acetate such as sodium acetate and potassium acetate. These bases can be used as a mixture thereof in a given ratio.

The amount of the base to be employed ranges usually from 0.05 to 2.0, preferably from 0.3 to 1.5 times mol., relative to the compound (III).

The amount of the 2,4-thiazolidinedione to be employed ranges usually from 1 to 5, preferably from 1 to 3 times mol., relative to the compound (III).

The reaction temperature in the condensation ranges usually from 40° C. to reflux temperature, preferably from 60° C. to reflux temperature.

The reaction time in the condensation ranges usually from 0.5 to 50 hours, preferably from 1 to 10 hours.

Reduction is carried out by catalytic hydrogenation in the above-described lower alcohol or organic solvent in the presence of a catalyst.

Examples of the catalyst includes palladium black, palladium-carbon, palladium-barium sulfate, palladium-barium carbonate, platinum oxide, platinum-carbon.

The reaction temperature in the reduction ranges usually from 0 to 180° C., preferably from 50 to 120° C.

The reaction time in the reduction ranges usually from 0.5 to 50 hours, preferably from 1 to 10 hours.

Although the reduction proceedes in a normal pressure, it is preferable to conduct the reduction under the pressure of not more than 150 kg/cm$^2$, preferably under the pressure ranging from 5 to 100 kg/cm$^2$.

Further, the reduction may be conducted in the presence of hydrochloric acid. In this case, the amount of hydrochloric acid to be employed ranges usually from 0.5 to 5, preferably from 0.5 to 1.5, more preferably from 0.5 to 1.1 times mol., relative to the compound (IV).

By the method of this invention, since the compound (III) can be produced in a high purity and in a high yield, the reaction mixture containing the compound (III) can be used for the subsequent reactions, i.e. condensation and reduction without purification.

The compound (v) which is obtained in the above-described manner, especially 5-[4-[2-(5-ethyl-2-pyridyl)ethoxy]benzyl]-2,4-thiazolidinedione is processed into hydrochloride by a per se known method, which is mixed with a physiologically acceptable carrier, excipient, binder, diluent, etc. And the mixture is administered either orally or non-orally as a pharmaceutical composition.

The dosage form for said pharmaceutical composition includes such oral dosage forms as granules, powders, tablets, capsules, syrups, emulsions, suspensions, etc. and such non-oral dosage forms as injections (e.g. subcutaneous, intravenous, intramuscular and intraperitoneal injections), drip infusions, external application forms (e.g. nasal spray preparations, transdermal preparations, ointments, etc.), and suppositories (e.g. rectal and vaginal suppositories).

These dosage forms can be manufactured by the per se known technique conventionally used in pharmaceutical procedures. The specific manufacturing procedures are as follows.

To manufacture an oral dosage form, an excipient (e.g. lactose, sucrose, starch, D-mannitol, etc)., a disintegrator (e.g. calcium carbonate, starch, carboxymethylcellulose calcium (carmellose calcium), low substituted hydroxypropylcellulose, crosscarmellose sodium, carboxymethyl starch sodium, light anhydrous silicic acid, etc.), a binder (e.g. pregelatinized starch, powdered acacia, carboxymethylcellulose, hydroxypropylcellulose, hydroxypropylmethylcellulose, polyvinylpyrrolidone, crystalline cellulose, etc.), and a lubricant (e.g. talc, magnesium stearate, calcium stearate, colloidal silica, polyethylene glycol 6000, etc.), for instance, are added to the active component and the resulting composition is compressed. Where necessary, acids such as hydrochloric acid, phosphoric acid, malonic acid, succinic acid, DL-malic acid, tartaric acid, maleic acid, fumaric acid, citric acid and etc.; and bases such as sodium carbonate, sodium hydrogencarbonate, sodium citrate, sodium tartrate and etc. may be added to the oral dosage forms for the purpose of promoting dissolution of the active component.

The oral dosage forms may be coated, by the per se known technique, for masking the taste or for enteric dissolution or sustained release. The coating material that can be used includes, for instance, enteric film coating polymers such as cellulose acetate phthalate, methacrylic acid copolymer L, methacrylic acid copolymer LD, methacrylic acid copolymer S, hydroxypropylmethylcellulose phthalate, hydroxypropylmethylcellulose acetate succinate, carboxymethylethylcellulose, and etc.; gastric film coating polymers such as polyvinylacetal diethylaminoacetate, aminoalkyl methacrylate copolymer E, and etc.; water soluble polymer such as hydroxypropylcellulose, hydroxypropylmethylcellulose, and etc.; water insoluble polymers such as ethylcellulose, aminoalkyl methacrylate copolymer RS, ethylacrylate methylmethacrylate copolymer, and etc.; wax, and etc. In the process of coating, plasticizers such as polyethyleneglycol and etc., and shading agents such as titanium dioxide, diiron trioxide and etc. may be used along with the above-described coating materials.

Injections can be manufactured typically by the following procedure. The active component is dissolved, suspended or emulsified in an aqueous vehicle (e.g. distilled water, physiological saline, Ringer's solution, etc.) or an oily vehicle (e.g. vegitable oil such as olive oil, sesame oil, cottonseed oil, corn oil, etc.; propylene glycol, etc.) together with a dispersant (e.g. Tween 80 (Atlas Powder, U.S.A.), HCO 60 (Nikko Chemicals, Japan), polyethylene glycol, carboxymethylcellulose (carmellose), sodium alginate, etc.), a preservative (e.g. methyl p-hydroxybenzoate, propyl p-hydroxybenzoate, benzyl alcohol, chlorobutanol, phenol, etc.), an isotonizing agent (e.g. sodium chloride, glycerol, D-sorbitol, D-mannitol, xylitol, glucose, fructose, etc.) and other additives. If desired, a solubilizer (e.g. sodium salicylate, sodium acetate, etc.), a stabilizer (e.g. human serum albumin), an analgesic agent (e.g. propylene glycol, lidocaine hydrochloride, benzyl alcohol, etc.) and other additives can also be added.

A dosage form for external application can be manufactured by processing the active component into a solid, semi-solid or liquid composition. To manufacture a solid composition, for instance, the active component, either as it is or in admixture with an excipient (e.g. lactose, D-mannitol, starch, crystalline cellulose, sucrose, etc.), a thickener (e.g. natural gums, cellulose derivatives, acrylic polymers, etc.), etc., are processed into powders. The liquid composition can be manufactured in substantially the same manner as the injections mentioned above. The semi-solid composition is preferably provided in a hydrous or oily gel form or an ointment form. These compositions may optionally contain a pH control agent (e.g. phosphoric acid, citric acid, hydrochloric acid, sodium hydroxide, etc.), and a preservative (e.g. p-hydroxybenzoic acid esters, chlorobutanol, benzalkonium chloride, etc.), among other additives.

Suppositories can be manufactured by processing the active component into an oily or aqueous composition, whether solid, semi-solid or liquid. The oleaginous base that can be used includes, for instance, higher fatty acid glycerides [e.g. cacao butter, Witepsols (huels Aktiengesellschaft, Germany), etc.], medium-chain fatty acid triglycerides [e.g. Migriols (huels Aktiengesellschaft, Germany), etc.], vegetable oils (e.g. sesame oil, soybean oil, cotton-seed oil, etc.), etc. The water-soluble base includes, for instance, polyethylene glycols, propylene glycol, etc. The hydrophilic base includes, for instance, natural gums, cellulose derivatives, vinyl polymers, and acrylic polymers, etc.

The pharmaceutical composition is low in toxicity and can be safely used in mammals (e.g. humans, mice, rats, rabbits, dogs, cats, bovines, horses, swines, monkeys) as an insulin sensitivity enhancer, especially a pharmaceutical composition for prophylaxis and treatment of diabetes.

The dosage of the pharmaceutical composition can be selected appropriately according to the recipient, the recipient's age and body weight, current clinical status, administration time, dosage form, and method of administration, among other factors. For example, the dosage for an adult can be selected from the oral dose range of 0.01 to 10 mg/kg body weight, preferably 0.05 to 10 mg/kg body weight, more preferably 0.05 to 5 mg/kg body weight; or the parenteral dose range of 0.005 to 10 mg/kg body weight, preferably 0.01 to 10 mg/kg body weight, more preferably 0.01 to 1 mg/kg body weight. The preferred frequency of administration is 1 to 3 times a day.

The present invention is hereinafter described in more detail by means of the following Reference Examples, Working Examples and Comparative Examples. It should be understood, however, that this invention is not restricted to these examples.

Elution in the column chromatography in Reference Examples, Working Examples and Comparative Examples was conducted under observation by TLC (Thin Layer Chromatography). In the observation of TLC, as the TLC plate, Kieselguhr 60F$_{254}$ manufactured by Merck & Co. was employed, as the developing solvent, the solvent used as eluent in the column chromatography was employed, and as detecting method, the UV detector (detecting wavelength: 254 nm) was employed. As silica gel for the column, Kieselguhr 60 (70 to 230 mesh) manufactured by Merck & Co, was employed.

Incidentally, the abbreviations used in Reference Examples and Working Examples have the following meanings.

s: singlet, d: doublet, t: triplet, q: quartet, d—d: double doublet, m: multiplet, Br: broad, J: coupling constant, Hz: Hertz, CDCl$_3$: heavy chloroform, TMS: tetramethyl silane, DMSO-d$_6$: heavy dimethyl sulfoxide.

REFERENCE EXAMPLE 1

Production of 2-(5-ethyl-2-pyridyl)ethyl methanesulfonate [hereinafter simply referred to as compound (a)]

2-(5-Ethyl-2-pyridine)ethanol (100 mmol., 15.1 g) was mixed with methylene chloride (150 ml), to which was added at room temperature triethylamine (120 mmol., 10.4 g). The mixture was cooled, to which was added dropwise at inner temperatures of about 10° C. methanesulfonyl chloride (103 mmol., 13.7 g). Then, the reaction was allowed to proceed for 3 hours at room temperature. After completion of the reaction, water (100 ml) was added to the reaction mixture. The organic layer and the aqueous layer were separated from each other. The aqueous layer was further subjected to extraction with methylene chloride (50 ml×2). The organic layers were combined, washed with a saturated aqueous solution of sodium hydrogencarbonate (100 ml) and a saturated aqueous solution of sodium chloride (100 ml), successively, dried over anhydrous sodium sulfate and, then, concentrated under reduced pressure to afford the compound (a) (22.0 g) (yield 97.0%).

$^1$H-NMR(CDCl$_3$,TMS,300 MHz) δ(ppm): 1.24(3H,t, J=7.6 Hz), 2.64(2H,q,J=7.6 Hz), 2.92(3H,s), 3.20(2H,t,J=6.5 Hz), 4.64(2H,t,J=6.5 Hz), 7.16(1H,d,J=7.9 Hz), 7.49(1H, d—d,J=7.9 Hz&2.2 Hz), 8.40(1H,d,J=2.2 Hz); IR(Neat) ν cm$^{-1}$: 1602, 1570, 1490, 1354, 1176.

REFERENCE EXAMPLE 2

Production of 2-(5-ethyl-2-pyridyl)ethyl p-toluenesulfonate [hereinafter simply referred to as compound (a')]

A mixture of 2-(5-ethyl-2-pyridine)ethanol (200 mmol., 30.2 g) and tetrahydrofuran (134 ml) was cooled to 10° C., to which was added a solution of sodium hydroxide (710 mmol., 28.4 g) in water (134 ml). This mixture was further cooled, to which was added dropwise, at inner temperatures ranging from 0 to 5° C., a solution of p-toluenesulfonyl chloride (258 mmol., 49.2 g) in tetrahydrofuran (202 ml), followed by allowing the reaction to proceed for further two hours at the same temperature range. After completion of the reaction, ice-water (400 ml) and ethyl acetate (400 ml) were added to the reaction mixture. The organic layer and the aqueous layer were separated from each other. The aqueous layer was subjected to further extraction with ethyl acetate (200 ml). The organic layers were combined and washed with water (400 ml×3), which was dried over anhydrous sodium sulfate, followed by concentration under reduced pressure to afford the compound (a') (59.9 g) (yield 98.1%).

$^1$H-NMR(CDCl$_3$,TMS,90 MHz) δ(ppm): 1.22(3H,t,J=7.2 Hz), 2.42(3H,s), 2.62(2H,q,J=7.2 Hz), 3.09(2H,t,J=6.3 Hz), 4.42(2H,t,J=6.3 Hz), 7.07(1H,d,J=7.2 Hz), 7.29(2H,d,J=8.1 Hz), 7.42(1H,d—d,J=7.2 Hz & 1.8 Hz), 7.71(2H,d,J=8.1 Hz), 8.27(1H,d,J=2.2 Hz); IR(Neat) ν cm$^{-1}$: 1605, 1500, 1362, 1176.

REFERENCE EXAMPLE 3

Production of a Toluene Solution of the Compound (a)

2-(5-Ethyl-2-pyridine)ethanol (622 mmol., 94.1 g) was mixed with toluene (400 ml). To the mixture were added, at room temperature, triethylamine (622 mmol., 62.8 g) and toluene (300 ml). The mixture was cooled with ice, to which was added dropwise, at inner temperatures around 10° C., methanesulfonyl chloride (676 mmol., 77.4 g) over 30 minutes. The reaction mixture was warmed to inner temperature of 30° C. over 15 minutes. The reaction was further allowed to proceed for 5 hours at the same temperature. After completion of the reaction, the reaction mixture was washed with water (450 ml×2), which was concentrated under reduced pressure to leave a toluene solution (273.4 g). The solution was diluted with toluene to give a toluene solution (600.9 g) of the compound (a), quantitatively.

REFERENCE EXAMPLE 4

Production of 5-[4-[2-(5-ethyl-2-pyridyl)ethoxy] benzylidene]-2,4-thiazolidinedione [hereinafter simply referred to as compound (d)]

The crude compound (c) produced in Working Example 4 described later [70.0 g, 62.1 g(243 mmol) when calculated in terms of pure compound], 2,4-thiazolidinedione (641 mmol. 75.1 g) and ethanol (1800 ml) were mixed. To this solution were added, at room temperature, piperidine (203 mmol., 17.3 g) and ethanol (230 ml). The mixture was heated under reflux for 5 hours at an inner temperature of 79° C. After completion of the reaction, the reaction mixture was cooled to 10° C. over a period of 3 hours. Then, the resulting crystalline precipitate was collected by filtration, which was washed with ethanol (300 ml) of 10° C. to give crude crystals of the compound (d). To the crude crystals was added ethanol (2600 ml). The mixture was stirred while heating under reflux, which was further cooled to 10° C., followed by stirring for 1.5 hour at the same temperature. The resulting crystalline product was collected by filtration, washed with ethanol (250 ml) and dried under reduced pressure to afford the compound (d) (66.3 g) [the yield from the compound (c) was 77.0%,and the overall yield from 2-(5-ethyl-2-pyridine)ethanol was 61.4%]. Spectrum data of the compound (d):

$^1$H-NMR(DMSO-d$_6$,TMS,90 MHz) δ(ppm): 1.14(3H,t,J= 7.2 Hz), 2.56(2H,q,J=7.2 Hz), 3.16(2H,t,J=6.3 Hz), 4.45 (2H,t,J=6.3 Hz), 7.08(2H,d,J=9.0 Hz), 7.28(1H,d,J=8.1 Hz), 7.49–7.65(3H,m), 7.73(1H,s), 8.38(1H,d,J=2.2 Hz); IR(Neat) ν cm$^{-1}$: 1708, 1602, 1512, 1258, 1182; MS(EI) (M+) 354; Elemental Analysis for: C$_{19}$H$_{18}$N$_2$O$_3$S; Calcd.: C; 64.39, H; 5.12, N; 7.90, S; 9.05; Found : C; 64.14, H; 4.91, N; 7.94, S; 9.11.

REFERENCE EXAMPLE 5

Production of a Toluene Solution of the Compound (a)

2-(5-Ethyl-2-pyridine)ethanol (200 mmol., 30.2 g) was mixed with toluene (224 ml), to which was added triethylamine (210 mmol., 21.3 g) at room temperature. This mixture solution was cooled, to which was added dropwise at inner temperatures of about 10° C. methanesulfonyl chloride (218 mmol., 25.0 g) over a period of 50 minutes. Then, the reaction was allowed to proceed for one hour at an inner temperature of 30° C. After completion of the reaction, the reaction mixture was washed with water (145 ml×2) to give a toluene solution of the compound (a) (237 g) quantitatively.

REFERENCE EXAMPLE 6

Production of the Compound (d)

The crude compound (c) produced in Working Example 5 described later [49.1 g, 38.8 g (152 mmol)when calculated in terms of pure compound] was mixed with 2,4-thiazolidinedione (182 mmol., 21.3 g) and methanol (624 ml). To this solution was added pyrrolidine (153 mmol., 10.9 g) at room temperature, and the reaction was allowed to proceed under stirring for 5 hours at an inner temperature of 45° C. After completion of the reaction, the reaction mixture was cooled to 40° C., to which was added dropwise conc. hydrochloric acid (148 mmol., 15.0 g) over a period of 30 minutes. The mixture was aged at the same temperature, and for further one hour at 15° C. The resulting crystalline precipitate was collected by filtration and washed with methanol (235 ml) to give crude crystals of the compound (d). To the crude crystals were added methanol (843 ml), water (59 ml) and triethylamine (243 mmol., 24.6 g). The mixture was stirred at 55° C. to make a solution. The solution was then cooled to 40° C., to which was added dropwise conc. hydrochloric acid (148 mmol., 15.0 g) over a period of 30 minutes. Then, the mixture was aged for 30 minutes at the same temperature and for further one hour at 5° C. The resulting crystalline precipitate was collected by filtration and washed with ethanol (202 ml), followed by drying under reduced pressure to afford the compound (d) (53.0 g). [The yield from the compound (c) was 95.0%, and the overall yield from 2-(5-ethyl-2-pyridine)ethanol was 75.0%).

Elemental Analysis for: C$_{19}$H$_{18}$N$_2$O$_3$S; Calcd.: C; 64.39, H; 5.12, N; 7.90, S; 9.05; Found : C; 64.32, H; 5.01, N; 7.98, S; 9.26.

REFERENCE EXAMPLE 7

Production of 5-[4-[2-(5-ethyl-2-pyridyl)ethoxy]benzyl]-2, 4-thiazolidinedione [hereinafter simply referred to as compound (e)]

A 1L-autoclave was charged with the compound (d) (84.6 mmol., 30 g), 5% palladium-carbon (50% hydrous, 30 g) and 1,4-dioxane (580 ml). Catalytic hydrogenation was conducted for 5 hours at 110° C. under hydrogen pressure of 50 Kg/cm . After completion of the reaction, the catalyst was filtered off when hot. The catalyst was washed with 1,4-dioxane (190 ml). The filtrate and the washing were combined and concentrated to a volume of 520 ml, followed by stirring for one hour at room temperature. The resulting crystalline product was collected by filtration, which was washed with 1,4-dioxane (95 ml) and ethanol (200 ml), successively. To this wet crystalline product was added 1,4-dioxane (400 ml), which was stirred under heating to dissolve the crystals, followed by stirring for 30 minutes at 90° C. The solution was stirred for further one hour at room temperature. The resulting crystalline product was washed with 1,4-dioxane (48 ml) and ethanol (200 ml), successively, followed by drying under reduced pressure to afford the compound (e) (20.6 g).

$^1$H-NMR(DMSO-d$_6$,TMS,300 MHz) δ(ppm): 1.18(3H,t, J=7.6 Hz), 2.59(2H,q,J=7.6 Hz), 3.00–3.35(4H,m), 4.30(2H, t,J=6.6 Hz), 4.86(1H,d—d,J=9.0 Hz&4.3 Hz), 6.86(2H,d,J= 8.5 Hz), 7.14(2H,d,J=8.5 Hz), 7.27(1H,d,J=8.0 Hz), 7.57 (1H,d—d,J=8.0 Hz&2.1 Hz), 8.36(1H,d,J=2.1 Hz), 11.99 (1H,br); IR(KBr) ν cm$^{-1}$: 1706, 1514, 1254.

REFERENCE EXAMPLE 8
Production of the Compound (e)

Substantially the same reaction as in Reference Example 7 was conducted, excepting using 10% palladium-carbon (50% hydrous, 22.5 g) in place of 5% palladium-carbon (50% hydrous, 30 g) and conducting the reaction under hydrogen pressure of 8.5 Kg/cm2 instead of 50 Kg/cm$^2$, to afford the compound (e) (22.0 g).

REFERENCE EXAMPLE 9
Production of the Compound (e)

A 1L-autoclave was charged with the compound (d) (84.6 mmol., 30 g), 5% palladium-carbon (50% hydrous, 30 g) and tetrahydrofuran (600 ml). Catalytic hydrogenation was conducted for 5 hours at 110° C. under hydrogen pressure of 50 Kg/cm After completion of the reaction, the catalyst was filtered off when hot, which was further washed with tetrahydrofuran (100 ml). The filtrate and the washing were combined and concentrated to a volume of 600 ml, followed by stirring for one hour at temperatures ranging from 0 to 10° C. The resulting crystalline product was collected by filtration and washed with tetrahydrofuran of 10° C. (100 ml). To this wet crystalline product was added tetrahydrofuran (1000 ml). The mixture was stirred while heating under reflux, which was left standing for cooling to room temperature. The solution was stirred for further one hour at temperatures ranging from 0 to 10° C. The resulting crystalline product was collected by filtration, which was washed with 10% tetrahydrofuran (100 ml), followed by drying under reduced pressure to afford the compound (e) (19.2 g).

REFERENCE EXAMPLE 10
Production of Hydrochloride of the Compound (e)

A 200 ml capacity four-necked flask was charged with the compound (e) produced in Reference Example 7 (9.0 g) and ethanol (94 ml). The mixture was stirred for 30 minutes under reflux, which was gradually cooled to room temperature, followed by stirring for further 30 minutes at the same temperature. The suspending crystals were collected by filtration and washed with ethanol (21 ml). Then, a 200 ml capacity four-necked flask was charged with the wet crystals and an ethanol solution of 10% hydrogen chloride gas (190 ml). The mixture was heated under reflux to make a solution, to which was added chelate resin (1.8 g). The mixture was stirred for one hour, to which was further added activated carbon (0.83 g). The mixture was stirred for 30 minutes, followed by filtering off the catalyst when hot. The catalyst was washed with ethanol (36 ml). The filtrate and the washing were combined and dissolved under reflux, followed by leaving standing for cooling to room temperature. The solution was aged for further one hour. The resulting crystalline product was collected by filtration, washed with ethanol (21 ml) and dried under reduced pressure to afford hydrochloride of the compound (e) (8.00 g).

$^1$H-NMR(DMSO-d$_6$,TMS,500 MHz) δ(ppm): 1.23(3H,t, J=7.7 Hz), 2.79(2H,q,J=7.7 Hz), 3.06(1H,d—d,J=14.1 Hz&9.0 Hz), 3.29(1H,d—d,J=14.1 Hz&4.3 Hz), 3.50(2H,t, J=6.4 Hz), 4.40(2H,t,J=6.4 Hz), 4.87(1H,d—d,J=9.0 Hz&4.3 Hz), 6.88(2H,d,J=8.6 Hz), 7.15(2H,d,J=8.6 Hz), 7.97(1H,d,J=8.1 Hz), 8.41(1H,d—d,J=8.1 Hz&2.0 Hz), 8.72 (1H,d,J=2.0 Hz), 12.03(1H,br); IR(KBr) ν cm : 1746, 1694, 1512, 1246; MS(EI) (M+) 356; Elemental Analysis for: $C_{19}H_{21}N_2O_3SCl$; Calcd.: C; 58.08, H; 5.39, N; 7.13, S; 8.16, Cl; 9.02; Found : C; 58.24, H; 5.37, N; 7.14, S; 8.15, Cl; 9.00.

REFERENCE EXAMPLE 11
Production of Hydrochloride of the Compound (e)

A 1000 ml capacity four-necked flask was charged with the compound (e) produced in Reference Example 7 (60.0 g) and 1N-HCl (360 ml). The mixture was stirred for 10 minutes at an inner temperature of 80° C. After the crystals were dissolved, insolubles were collected by filtration when hot, which were then washed with 1N-HCl (70 ml). The filtrate and the washing were combined and stirred for 10 minutes at an inner temperature of 80° C. to dissolve the crystals. The solution was gradually cooled to room temperature, which was aged for one hour at the same temperature. The resulting crystalline product was collected by filtration, washed with ethanol (140 ml) and dried under reduced pressure to afford hydrochloride of the compound (e) (56.4 g).

REFERENCE EXAMPLE 12
Production of Hydrochloride of the Compound (e)

A 1000 ml four-necked flask was charged with the compound (e) produced in Reference Example 7 (60.0 g), 2N-HCl (180 ml) and ethanol (180 ml). The mixture was stirred for 10 minutes while heating under reflux. After the crystals were dissolved, chelate resin (12.0 g) was added to the solution, and the mixture was stirred for one hour. To the mixture was further added activated carbon (4.15 g), which was stirred for 30 minutes, followed by filtering off the catalyst when hot. The catalyst was washed with a mixture of 2N-HCl (35 ml) and ethanol (35 ml). The filtrate and the washing were combined and stirred for 10 minutes under reflux to dissolve crystals. The solution was cooled gradually to room temperature, which was aged for further one hour at the same temperature. The resulting crystalline precipitate was collected by filtration, washed with ethanol (140 ml) and dried under reduced pressure to give hydrochloride of the compound (e) (56.4 g).

REFERENCE EXAMPLE 13
Production of the Compound (e)

A 1L-autoclave was charged with the compound (d) (63.48 mmol, 22.5 g), 20% palladium-carbon (50% hydrous, 11.25 g), 36% hydrochloric acid (5.45 ml) and methanol (423 ml). Catalytic hydrogenation was conducted for 6 hours at 100° C. under hydrogen pressure of 8.5 kg/cm$^2$. After completion of the reaction, the catalyst was filtered off under pressure, which was washed with methanol (1155 ml). The filtrate and the washing were combined, which was adjusted to pH 6 with 10% aqueous solution of sodium hydroxide and concentrated to an amount of 712. 5 g, followed by stirring for one hour at about 5° C. The resulting crystalline product was collected by filtration and washed with methanol (225 ml). To this wet crystalline product was added tetrahyrofuran (360 ml). The mixture was suspended for 30 minutes while heating under reflux, which was cooled to 5° C. over 3 hours, followed by stirring for one hour at 5° C. The resulting crystalline product was collected by filtration, which was washed with tetrahydrofuran (20.3 ml) and ethanol (45 ml) successively, followed by drying under reduced pressure to afford the compound (e) (18.1 g).

REFERENCE EXAMPLE 14

A fluidized-bed granulating and drying machine (produced by Powerex, Japan) was charge with 2479.5 g of hydrochloride of the compound (e).(2250 g in terms of the compound (e)), 13930.5 g of lactose and 540 g of carmellose calcium, followed by mixing at the preheating temperature and spraying 7500 g of an aqueous solution containing 450 g of hydroxypropylcellulose to yield granules. 16820 g of the granules were processed with cutter-mill (produced by Showa Kagaku Kikai Kousakusho, Japan) to yield milled granules. 16530 g of the milled granules, 513 g of carmellose calcium and 57 g of magnesium stearate were mixed to yield lubricated powders by using tumbling mixer (produced by Showa Kagaku Kikai Kousakusho, Japan). 16800 g of the lubricated powders were tabletted by using tabletting machine (produced by Kikusui Seisakusho, Japan) to yield 140000 tablets having the following formula and each containing 15 mg of the compound (e).

| Formula per table (unit: mg): | |
|---|---|
| 1) Hydrochloride of the compound (e) | 16.53 |
| 2) Lactose | 92.87 |
| 3) Carmellose calcium | 7.2 |
| 4) Hydroxypropylcellulose | 3.0 |
| 5) Magnesium stearate | 0.4 |
| Total | 120.0 |

REFERENCE EXAMPLE 15

In substantially the same manner as in Reference Example 14, 140000 tablets having the following formula and each containing 30 mg of the compound (e) were obtained.

| Formula per table (unit: mg): | |
|---|---|
| 1) Hydrochloride of the compound (e) | 33.06 |
| 2) Lactose | 76.34 |
| 3) Carmellose calcium | 7.2 |
| 4) Hydroxypropylcellulose | 3.0 |
| 5) Magnesium stearate | 0.4 |
| Total | 120.0 |

REFERENCE EXAMPLE 16

In substantially the same manner as in Reference Example 15, 140000 tablets having the following formula and each containing 45 mg of the compound (e) were obtained.

| Formula per table (unit: mg): | |
|---|---|
| 1) Hydrochloride of the compound (e) | 49.59 |
| 2) Lactose | 114.51 |
| 3) Carmellose calcium | 10.8 |
| 4) Hydroxypropylcellulose | 4.5 |
| 5) Magnesium stearate | 0.6 |
| Total | 180.0 |

WORKING EXAMPLE 1

Production of 4-[2-(5-ethyl-2-pyridyl)ethoxy]benzaldehyde [hereinafter simply referred to as compound (c)]

The compound (a) produced in Reference Example 1 (43.6 mmol., 10.0 g) was mixed with p-hydroxybenzaldehyde (74.1 mmol., 9.05 g), potassium carbonate (74.1 mmol., 10.2 g) and ethanol(50 volume %)/toluene(50 volume %) (100 ml). The mixture was heated for 5 hours at 80° C. under reflux. After completion of the reaction, the reaction mixture was concentrated under reduced pressure. To the concentrate was added ethyl acetate. The mixture was washed with 0.2N aqueous solution of sodium hydroxide and water, successively, followed by separating. The organic layer was dried over anhydrous sodium sulfate, and concentrated under reduced pressure. The concentrate was purified by subjecting to a silica gel column chromatography (eluent: toluene/ethyl acetate) to afford the compound (c) (yield 8.76 g, 78.9%). Spectrum data of the compound (c):

$^1$H-NMR(CDCl$_3$,TMS,300 MHz) δ(ppm): 1.27(3H,t,J= 7.6 Hz), 2.64(2H,q,J=7.6 Hz), 3.27(2H,t,J=6.7 Hz), 4.45 (2H,t,J=6.7 Hz), 7.00(2H,d,J=8.8 Hz), 7.20(1H,d,J=7.9 Hz), 7.48(1H,d—d,J=7.9 Hz&2.2 Hz), 7.81(2H,d,J=8.8 Hz), 8.41 (1H,d,J=2.2 Hz), 9.86(1H,s); IR(Neat) ν cm$^-$: 1692, 1602, 1578, 1258, 1162.

WORKING EXAMPLE 2

Production of the Compound (c)

Substantially the same reaction as in Working Example 1 was conducted, excepting employing ethanol in place of ethanol(50 volume %)/toluene(50 volume %), to afford the compound (c) (yield 6.88 g, 62.0%).

WORKING EXAMPLE 3

Production of the Compound (c)

Substantially the same reaction as in Working Example 1 was conducted, excepting employing the compound (a') produced in Reference Example 2 (43.6 mmol., 13.3 g) in place of the compound (a) (43.6 mmol., 10.0 g) and using ethanol in place of ethanol(50 volume %)/toluene(50 volume %), to afford the compound (c) (yield 7.41 g, 66.8%).

WORKING EXAMPLE 4

Production of the Compound (c)

To 594.9 g (containing 620 mmol.) of a toluene solution of the compound (a) produced in Reference Example 3 were added toluene (180 ml), p-hydroxybenzaldehyde (1054 mmol., 128.7 g) and ethanol (280 ml), which was made into a solution. To this solution were added potassium carbonate (1054 mmol., 145.7 g) and ethanol (420 ml). The mixture was refluxed for 5 hours at an inner temperature of 79° C. After completion of the reaction, the reaction mixture was concentrated under reduced pressure. To the concentrate were added toluene (700 ml) and a 0.2N aqueous solution of sodium hydroxide (560 ml), followed by separating. The organic layer was washed with a 0.2N aqueous solution of sodium hydroxide (560 ml) and water (560 ml), successively, to which was further added activated carbon (7.0 g). The mixture was stirred for one hour, then the activated carbon was filtered off. The filtrate was concentrated under reduced pressure to give a crude product of the compound (c) (142.4 g). In the crude product, 126.3 g of the compound (c) was contained, which was confirmed by means of HPLC. The yield from the compound (a) was 79.8%.

WORKING EXAMPLE 5

Production of the Compound (c)

To 237 g (containing 200 mmol.) of a toluene solution of the compound (a) produced in Reference Example 5 were added p-hydroxybenzaldehyde (340 mmol., 41.5 g) and 2-propanol (224 ml). The mixture was made into a solution. To this solution were added potassium carbonate (340 mmol., 47.0 g) and water (13.4 ml). The mixture was refluxed for 5 hours at an inner temperature of 79° C. After completion of the reaction, the reaction mixture was concentrated under reduced pressure. To the concentrate were added toluene (224 ml) and a 1N aqueous solution of sodium hydroxide (360 ml), followed by separating. The organic layer was washed with water (360 ml), to which was further added activated carbon (2.26 g). The mixture was stirred for 15 minutes, then the activated carbon was filtered off. The filtrate was concentrated under reduced pressure to leave a crude product of the compound (c) (51.0 g). In the crude product, 40.3 g of the compound (c) was contained, which was confirmed by means of HPLC. The yield from the compound (a) was 79.0%.

COMPARATIVE EXAMPLE 1

Substantially the same reaction as in Working Example 1, excepting using toluene in place of ethanol(50 volume %)/toluene(50 volume %) and conducting the reaction at 110° C. for 14 hours, was conducted to afford the compound (c) (yield 3.20 g, 28.8%).

In this case, 5-ethyl-2-vinylpyridine was produced as the secondary product, which was confirmed by isolation by means of a silica gel column chromatography. Spectrum data of 5-ethyl-2-vinylpyridine:

$^1$H-NMR(CDCl$_3$,TMS,300 MHz) δ(ppm): 1.25(3H,t,J= 7.6 Hz), 2.64(2H,q,J=7.6 Hz), 5.43(1H,d,J=10.9 Hz), 6.14 (1H,d,J=17.5 Hz), 6.81(1H,d—d,J=17.5 Hz&10.9 Hz), 7.23 (1H,d,J=8.0 Hz), 7.49(1H,d—d,J=8.0 Hz&2.2 Hz), 8.42(1H, d,J=2.2 Hz); IR(Neat) ν cm$^{-1}$: 1558, 1484, 1456, 1386, 1026; MS(EI) (M+) 133.

COMPARATIVE EXAMPLE 2

Substantially the same reaction as in Working Example 1, excepting using ethane dichloride in place of ethanol(50 volume %)/toluene(50 volume %) and conducting the reaction at 85° C. for 30 hours, was conducted to afford the compound (c) (yield 4.26 g, 38.4%).

In this case, 5-ethyl-2-vinylpyridine was produced as the secondary product, which was confirmed by isolation by means of a silica gel column chromatography.

COMPARATIVE EXAMPLE 3

Substantially the same reaction as in Working Example 3, excepting using tetrahydrofuran in place of ethanol and conducting the reaction at 70° C. for 45.5 hours, was conducted to afford the compound (c) (yield 4.02 g, 36.2%).

COMPARATIVE EXAMPLE 4

Substantially the same reaction as in Working Example 3, excepting using ethane dichloride in place of ethanol and conducting the reaction at 85° C. for 30 hours, was conducted to afford the compound (c) (yield 3.39 g, 30.5%).

According to the present invention, benzaldehyde compounds, which are useful as starting compounds for producing thiazolidinedione derivatives having hypoglycemic and hypolipidemic activities, can be produced conveniently in a high yield and high purity and in a relatively short reaction time.

Furthermore, the compound (III) can be produced in the manner of one-pot from the starting compounds for producing the compound (I), for example, 2-(5-ethyl-2-pyridine) ethanol described in the afore-described Reference Example 1 and the compound (II).

Moreover, according to the present invention, since the compound (III) of a high purity is obtained, a reaction mixture containing the compound (III) can be used for the subsequent reaction step without subjecting the reaction mixture to isolating or refining process specially.

What is claimed is:
1. A method of producing a compound having the formula

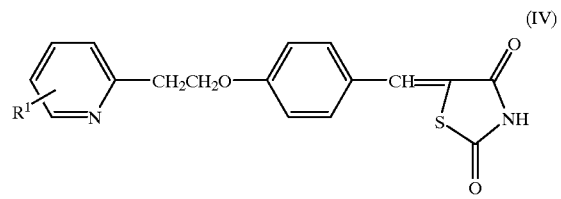

comprising reacting a compound having the formula

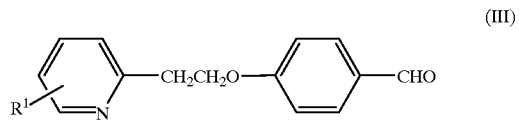

wherein R$^1$ stands for hydrogen or an optionally substituted alkyl or acyl group with 2,4-thiazolidinedione, wherein the compound having formula (III) is prepared by a method comprising reacting a compound represented by the formula:

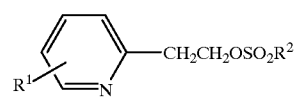

wherein R$^1$ has the same meaning as defined above, and R$^2$ stands for an optionally halogenated alkyl group or an optionally substituted phenyl group with a compound represented by the formula:

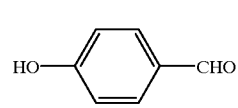

In a solvent comprising a lower alcohol or a mixture of a lower alcohol and an organic solvent other than an alcohol, in the presence of an alkali metal carbonate, or alkaline earth metal carbonate.

2. The method of claim 1, wherein R$^1$ is 5-ethyl.
3. The method of claim 1, wherein the lower alcohol is a C$_{1-3}$ alcohol.
4. The method of claim 3, wherein the alcohol is ethanol or 2-propanol.
5. The method of claim 1, wherein the reaction of the compound having formula (I) with the compound having formula (II) is conducted in a mixture of a lower alcohol and an organic solvent other than an alcohol.
6. The method of claim 5, wherein the organic solvent is selected from aromatic hydrocarbons, aliphatic hydrocarbons, esters, ethers, ketones, nitriles or amides.
7. The method of claim 6, wherein the organic solvent is toluene or ethyl acetate.

8. The method of claim 1, wherein the alkali metal carbonate is potassium carbonate.

9. The method of claim 1, wherein the reaction of the compound having formula (I) with the compound having formula (II) is conducted in the presence of water.

10. The method of claim 1, wherein the reaction of the compound having formula (I) with the compound having formula (II) is conducted at 70 to 90° C., in a solvent comprising ethanol or 2-propanol, in the presence of potassium carbonate and water, wherein the water is present in an amount of 1 to 10 volume % relative to the solvent.

11. The method of claim 5, wherein the lower alcohol is 2-propanol and the organic solvent is toluene.

12. The method of claim 11, wherein the reaction of the compound having formula (I) with the compound having formula (II) is conducted in the presence of water.

13. The method of claim 11, wherein the reaction of the compound having formula (I) with the compound having formula (II) is conducted in the presence of an alkali metal carbonate.

14. The method of claim 13, wherein the alkali metal carbonate is potassium carbonate.

15. The method of claim 1, wherein the reaction of the compound having formula (I) with the compound having formula (II) is conducted at 70 to 90° C., in a solvent comprising 2-propanol and toluene, in the presence of potassium carbonate and water, wherein the water is present in an amount of 1 to 10 volume % relative to the volume of solvent.

16. The method of claim 15, wherein $R^1$ is 5-ethyl.

17. The method of claim 5, wherein the solvent comprises at least 30 volume % of said lower alcohol.

18. The method of claim 17, wherein the solvent comprises at least 50 volume % of said lower alcohol.

19. The method of claim 15, wherein the solvent comprises 50 volume % propanol and 50 volume % toluene.

20. A method of producing a compound of the formula:

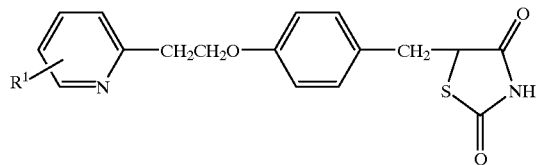

(V)

wherein $R^1$ stands for hydrogen or an optionally substituted alkyl or acyl group, said method comprising reacting a compound represented by the formula:

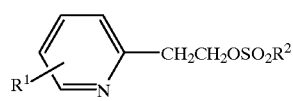

(I)

wherein $R^1$ has the same meaning as defined above, and $R^2$ stands for an optionally halogenated alkyl group or an optionally substituted phenyl group, with a compound represented by the formula:

(II)

in a solvent comprising a lower alcohol or a mixture of a lower alcohol and an organic solvent other than an alcohol, in the presence of an alkali metal carbonate, or alkaline earth metal carbonate, to form a compound of the formula:

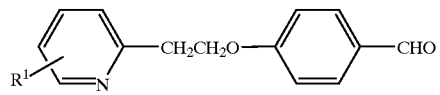

(III)

wherein $R^1$ is defined above, reacting the compound of formula (III) with 2,4-thiazolidinedione, to form a compound of the formula:

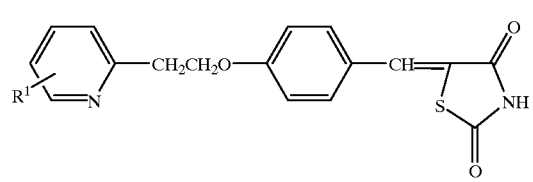

(IV)

and reducing the compound having the formula (IV).

21. The method of claim 20, wherein $R^1$ is 5-ethyl group.

22. The method of claim 20, wherein the lower alcohol is a $C_{1-3}$ alcohol.

23. The method of claim 22, wherein the alcohol is ethanol or 2-propanol.

24. The method of claim 20, wherein the reaction of the compound having formula (I) with the compound having formula (II) is conducted in a mixture of a lower alcohol and an organic solvent other than an alcohol.

25. The method of claim 24, wherein the organic solvent is selected from aromatic hydrocarbons, aliphatic hydrocarbons, esters, ethers, ketones, nitriles or amides.

26. The method of claim 25, wherein the organic solvent is toluene or ethyl acetate.

27. The method of claim 20, wherein the alkali metal carbonate is potassium carbonate.

28. The method of claim 20, wherein the reaction of the compound having formula (I) with the compound having formula (II) is conducted in the presence of water.

29. The method of claim 20, wherein the reaction of the compound having formula (I) with the compound having formula (II) is conducted at 70 to 90° C., in a solvent comprising ethanol or 2-propanol, in the presence of potassium carbonate and water, wherein the water is present in an amount of 1 to 10 volume % relative to the solvent.

30. The method of claim 24, wherein the lower alcohol is 2-propanol and the organic solvent is toluene.

31. The method of claim 30, wherein the reaction of the compound having formula (I) with the compound having formula (II) is conducted in the presence of water.

32. The method of claim 30, wherein the reaction of the compound having formula (I) with the compound having formula (II) is conducted in the presence of an alkali metal carbonate.

33. The method of claim 32, wherein the alkali metal carbonate is potassium carbonate.

34. The method of claim 20, wherein the reaction of the compound having formula (I) with the compound having formula (II) is conducted at 70 to 90° C., in a solvent comprising 2-propanol and toluene, in the presence of potassium carbonate and water, wherein the water is present in an amount of 1 to 10 volume % relative to the volume of solvent.

35. The method of claim 34, wherein $R^1$ is 5-ethyl.

36. The method of claim 24, wherein the solvent comprises at least 30 volume % of said lower alcohol.

37. The method of claim 36, wherein the solvent comprises at least 50 volume % of said lower alcohol.

38. The method of claim 34, wherein the solvent comprises 50 volume % propanol and 50 volume % toluene.

39. A method of producing a compound having the formula

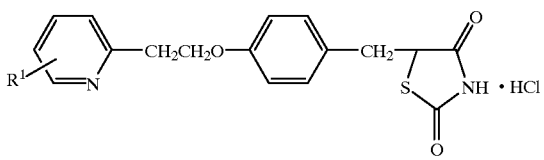

wherein $R^1$ stands for hydrogen or an optionally substituted alkyl or acyl group, said method comprising:
reacting a compound represented by the formula:

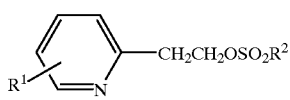

(I)

wherein $R^1$ has the same meaning as defined above, and $R^2$ stands for an optionally halogenated alkyl group or an optionally substituted phenyl group, with a compound represented by the formula:

(II)

in a solvent comprising a lower alcohol or a mixture of a lower alcohol and an organic solvent other than an alcohol, in the presence of an alkali metal carbonate, or alkaline earth metal carbonate, to form a compound of the formula:

(III)

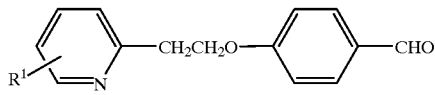

wherein $R^1$ is defined above, and reacting the compound of formula (III) with 2,4-thiazolidinedione, to form a compound of the formula:

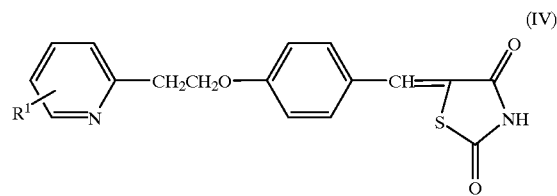

reducing the compound of formula (IV) to form the compound of formula:

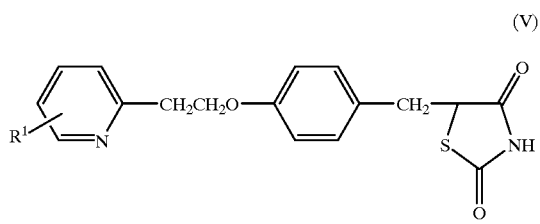

and processing the compound of formula (V) into hydrochloride.

40. The method of claim 39, wherein $R^1$ is 5-ethyl group.

41. The method of claim 39, wherein the lower alcohol is a $C_{1-3}$ alcohol.

42. The method of claim 41, wherein the alcohol is ethanol or 2-propanol.

43. The method of claim 39, wherein the reaction of the compound having formula (I) with the compound having formula (II) is conducted in a mixture of a lower alcohol and an organic solvent other than an alcohol.

44. The method of claim 43, wherein the organic solvent is selected from aromatic hydrocarbons, aliphatic hydrocarbons, esters, ethers, ketones, nitriles or amides.

45. The method of claim 44, wherein the organic solvent is toluene or ethyl acetate.

46. The method of claim 39, wherein the alkali metal carbonate is potassium carbonate.

47. The method of claim 39, wherein the reaction of the compound having formula (I) with the compound having formula (II) is conducted in the presence of water.

48. The method of claim 39, wherein the reaction of the compound having formula (I) with the compound having formula (II) is conducted at 70 to 90° C., in a solvent comprising ethanol or 2-propanol, in the presence of potassium carbonate and water, wherein the water is present in an amount of 1 to 10 volume % relative to the solvent.

49. The method of claim 43, wherein the lower alcohol is 2-propanol and the organic solvent is toluene.

50. The method of claim 49, wherein the reaction of the compound having formula (I) with the compound having formula (II) is conducted in the presence of water.

51. The method of claim 49, wherein the reaction of the compound having formula (I) with the compound having formula (II) is conducted in the presence of an alkali metal carbonate.

52. The method of claim 51, wherein the alkali metal carbonate is potassium carbonate.

53. The method of claim 39, wherein the reaction of the compound having formula (I) with the compound having formula (II) is conducted at 70 to 90° C., in a solvent comprising 2-propanol and toluene, in the presence of potassium carbonate and water, wherein the water is present in an amount of 1 to 10 volume % relative to the volume of solvent.

54. The method of claim 53, wherein $R^1$ is 5-ethyl.

55. The method of claim 43, wherein the solvent comprises at least 30 volume % of said lower alcohol.

56. The method of claim 55, wherein the solvent comprises at least 50 volume % of said lower alcohol.

57. The method of claim 53, wherein the solvent comprises 50 volume % propanol and 50 volume % toluene.

* * * * *